(12) United States Patent
Samsoondar

(10) Patent No.: US 7,108,833 B2
(45) Date of Patent: *Sep. 19, 2006

(54) SAMPLE TAB

(75) Inventor: James Samsoondar, Cambridge (CA)

(73) Assignee: Spectromedical Inc., Cambridge (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/981,765

(22) Filed: Nov. 5, 2004

(65) Prior Publication Data

US 2005/0170522 A1 Aug. 4, 2005

Related U.S. Application Data

(63) Continuation-in-part of application No. 10/929,887, filed on Aug. 31, 2004, now abandoned, which is a continuation-in-part of application No. 09/958,933, filed on Jan. 23, 2002, now Pat. No. 6,582,964, which is a continuation-in-part of application No. 10/042,258, filed as application No. PCT/CA00/00549 on May 11, 2000, now Pat. No. 6,841,132.

(60) Provisional application No. 60/133,876, filed on May 12, 1999.

(30) Foreign Application Priority Data

Oct. 8, 2004 (CA) .................................. 2484309
Oct. 15, 2004 (EP) .............................. 04256382.5

(51) Int. Cl.
*B01L 3/00* (2006.01)

(52) U.S. Cl. ................ 422/102; 422/99; 422/58; 436/164; 436/165; 435/288.3

(58) Field of Classification Search ............ 422/82.05, 422/82.09, 99, 102, 104, 939, 940, 58; 436/164, 436/165, 169; 600/573; 435/288.3, 288.7
See application file for complete search history.

(56) References Cited

U.S. PATENT DOCUMENTS

| | | | | |
|---|---|---|---|---|
| 3,741,377 A | * | 6/1973 | Krellen | 206/5 |
| 4,387,972 A | * | 6/1983 | Valencia | 359/398 |
| 4,535,778 A | * | 8/1985 | Kitrilakis et al. | 600/349 |
| 4,791,938 A | * | 12/1988 | Van Valkenburg | 600/576 |
| 5,207,984 A | * | 5/1993 | Kheiri | 422/58 |
| 5,800,781 A | * | 9/1998 | Gavin et al. | 422/73 |
| 5,863,791 A | | 1/1999 | Baldszun et al. | |
| 6,582,964 B1 | * | 6/2003 | Samsoondar et al. | 436/67 |
| 6,841,132 B1 | * | 1/2005 | Samsoondar | 422/102 |
| 2005/0019936 A1 | * | 1/2005 | Samsoondar et al. | 436/80 |
| 2005/0133382 A1 | * | 6/2005 | Gerard et al. | 206/5.1 |

FOREIGN PATENT DOCUMENTS

| | | |
|---|---|---|
| DE | 40 21 855 A1 | 1/1992 |
| EP | 1 102 057 A1 | 5/2001 |
| FR | 2 714 183 A1 | 6/1995 |

OTHER PUBLICATIONS

European Search Report dated Jan. 3, 2006 issued in counterpart European Application No. 04256382.5.

* cited by examiner

*Primary Examiner*—Maureen M. Wallenhorst
(74) *Attorney, Agent, or Firm*—Arent Fox PLLC

(57) ABSTRACT

A sample tab for retaining a sample during spectroscopic analysis includes a base plate, a sample well, and a cover plate. The sample well may vary in size to accommodate different sample volumes, and the base of the sample well may be positioned above or below the plane of the base plate. The walls of the sample well may also include one, or more than one overflow opening for draining excess sample, and an overflow channel to retain the excess sample.

33 Claims, 9 Drawing Sheets

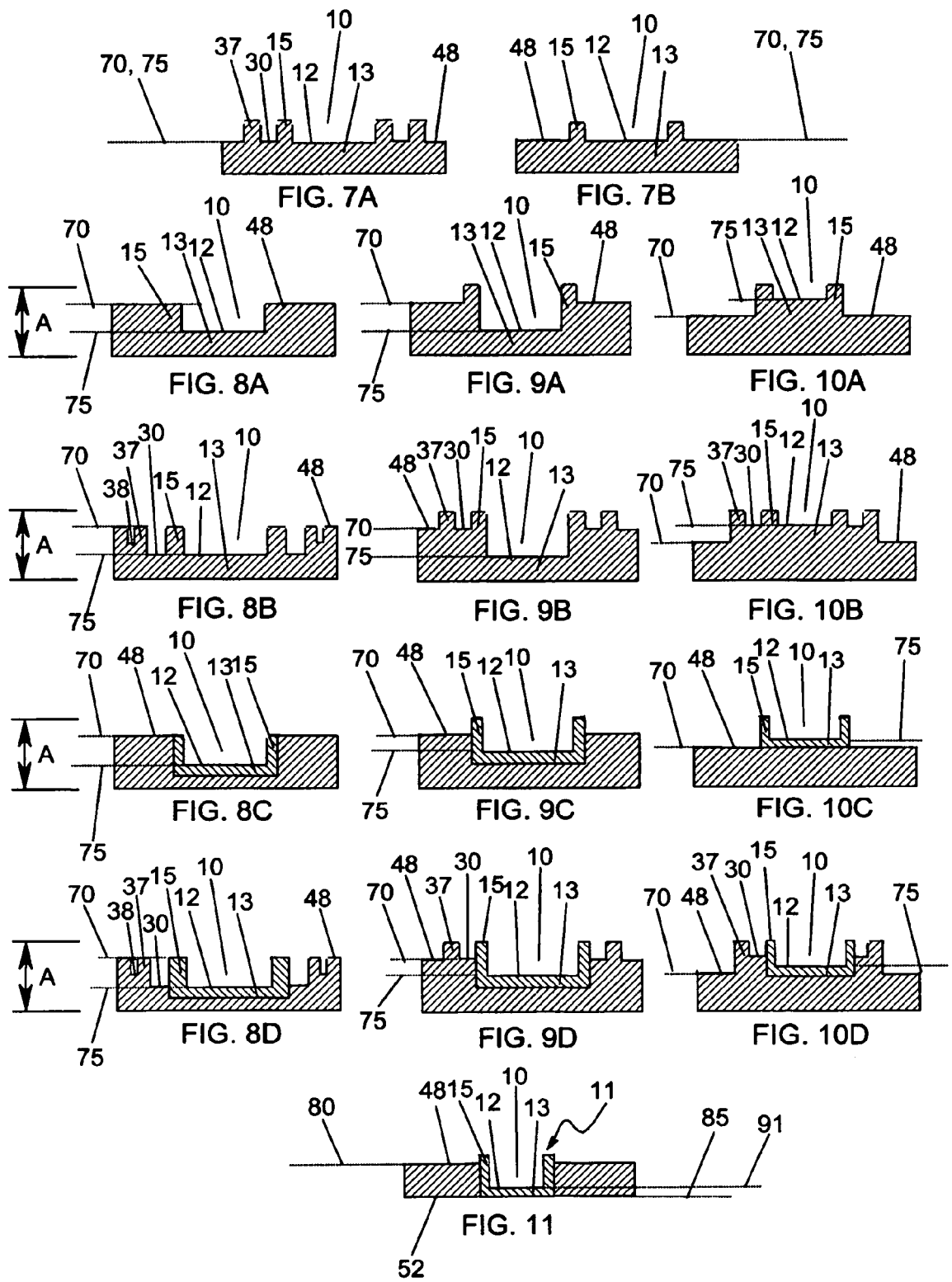

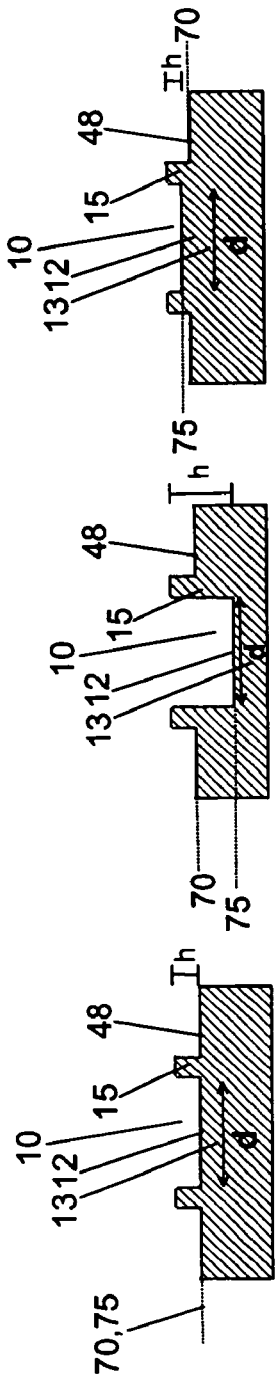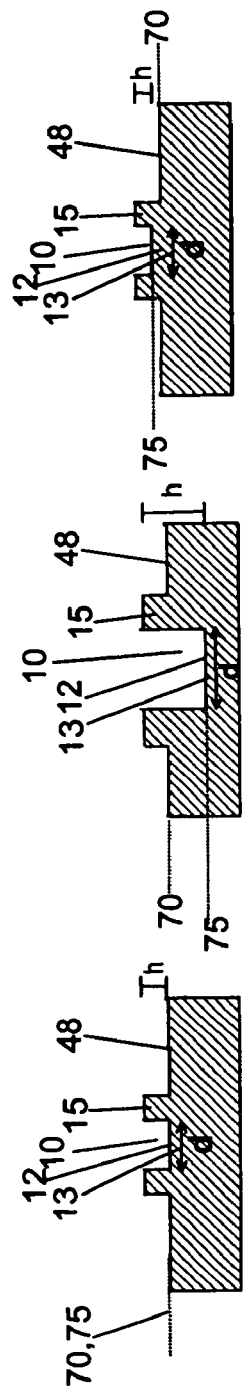
FIG. 12A  FIG. 12B  FIG. 12C
FIG. 13A  FIG. 13B  FIG. 13C
FIG. 14A  FIG. 14B  FIG. 14C

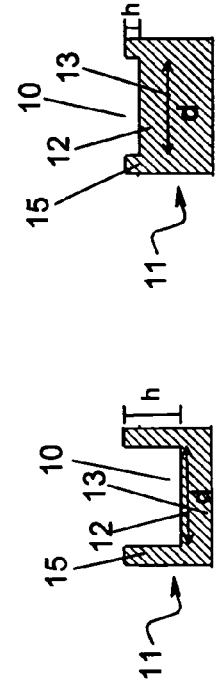
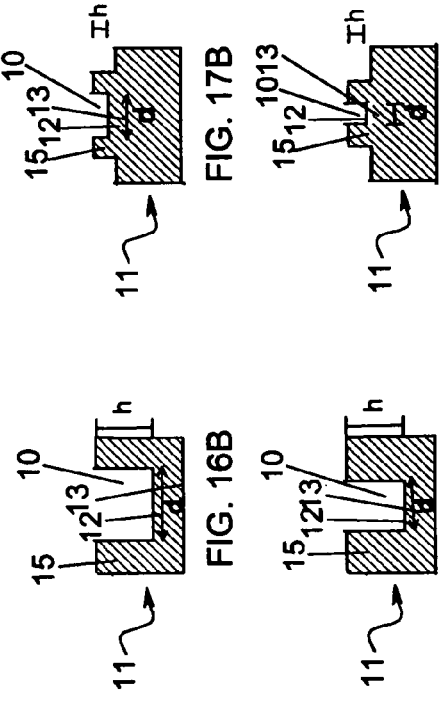
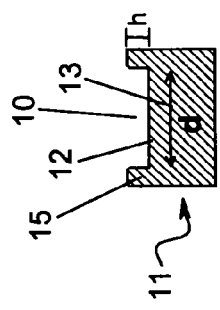
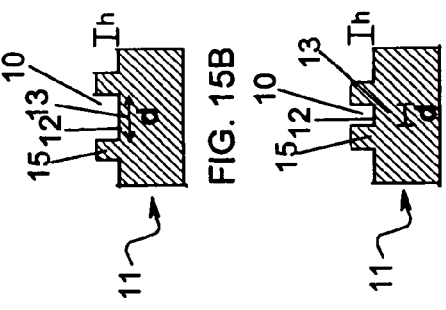

SAMPLE TAB

This application is a Continuation-in-Part Application of U.S. application Ser. No. 10/929,887, filed Aug. 31, 2004, now abandoned, which is a Continuation-in-Part of U.S. application Ser. No. 10/042,258, filed Jan. 11, 2002, now U.S. Pat. No. 6,841,132, issued on Jan. 11, 2005, which is a Continuation-in-Part of U.S. application Ser. No. 09/958,933 filed on Jan. 23, 2002, now U.S. Pat. No. 6,582,964, issued on Jun. 24, 2003, which is the National Stage of International Application No. PCT/CA00/00549, filed on May 11, 2000, which claims priority to U.S. Provisional Application No. 60/133,876, filed May 12, 1999.

FIELD OF THE INVENTION

The invention relates to a tab for retaining a sample for analysis. More particularly, the present invention provides an apparatus and method for sample analysis using a variety of instruments including spectroscopic or microscopic analysis.

BACKGROUND OF THE INVENTION

Rapid methods for analysis of a compound or a substance of interest within a biological or non-biological sample are desired within the art.

For example, U.S. Pat. Nos. 4,575,240, 4,134,678 and 4,734,260 disclose sample chambers for fluid analysis within automated analysers. In U.S. Pat. No. 4,575,240, the sample chamber is complex comprising input and output ports for adding a fluid sample into a reservoir formed within a prism that is sealed against a window through which light passes through. A spring attached to a door of the chamber is provided so that when the door is closed, the spring urges the prism against a sealing member. U.S. Pat. No. 4,134,678 discloses an, on-line cuvette that can be use within an automated analyser comprising sample input and output ports.

U.S. Pat. No. 4,734,260 discloses a cuvette for liquid sample analysis comprising a thin sample chamber delimited by radiation transmitting members. The chamber is made from a plurality of component parts that when assembled form the cuvette. Ports extend into, and out of, the sample chamber for sample injection and withdrawal. The ports pass through a housing and one of the radiation transmitting members. Plugs are provided to seal the ports after a sample has been introduced into the cuvette.

U.S. Pat. No. 5,430,542 discloses a simplified disposable cuvette made of two transparent plastic cover sheets that are adhesively attached to a third thicker plastic sheet comprising a sample cavity. The disposable cuvette comprises input and output ports, with the input port adapted to be attached to a syringe for sample introduction. Again, only fluid samples may be analysed using this disposable cuvette.

There is a need for a sample chamber that is easy to use and adaptable for a range of applications, including the analysis, of semi-solid and fluid samples. It is an object of the present invention to overcome disadvantages of the prior art.

The above object is met by a combination of the features of the main claims.

The sub claims disclose further advantageous embodiments of the invention.

SUMMARY OF THE INVENTION

The present invention relates to a sample tab for retaining a sample for analysis.

The present invention provides a sample tab comprising:
a base plate having a top surface and a bottom surface, the top surface of the base plate defining a first plane;
a well disposed on a section of the base plate, the well having a side wall and a bottom wall, wherein a top surface of the bottom wall defines a second plane, the second plane disposed above or below the first plane, and
a cover plate hingedly connected to the base plate, the cover plate having an open position allowing a sample to be introduced into the well and a closed position in which a bottom surface of a section of the cover plate covers the well,
wherein at least a portion of the bottom wall of the well is transparent or translucent, and wherein at a least a portion of one of the section of the cover plate and the section of the base plate is transparent or translucent, and at least a portion of the other of the section of the cover plate and the section of the base plate is transparent, translucent or reflective, or
wherein the bottom wall of the well is defined by the section of the base plate, and wherein at least a portion of one of the section of the cover plate and the section of the base plate is transparent or translucent, and at least a portion of the other of the section of the cover plate and the section of the base plate is transparent, translucent, or reflective.

The present invention also provides a set or combination of two, or more than two sample tabs, wherein each of the two, or more than two sample tabs comprises:
a base plate having a top surface and a bottom surface, the top surface of the base plate defining a first plane;
a well disposed on a section of the base plate, the well having a side wall and a bottom wall, wherein a top surface of the bottom wall defines a second plane, the second plane disposed above the first plane, below the first plane, or coincident with the first plane, and
a cover plate hingedly connected to the base plate, the cover plate having an open position allowing a sample to be introduced into the well and a closed position in which a bottom surface of a section of the cover plate covers the well,
wherein at least a portion of the bottom wall of the well is transparent or translucent, and wherein at least a portion of one of the section of the cover plate and the section of the base plate is transparent or translucent, and at least a portion of the other of the section of the cover plate and the section of the base plate is transparent, translucent or reflective, or
wherein the bottom wall of the well is defined by the section of the base plate, and wherein at least a portion of one of the section of the cover plate and the section of the base plate is transparent or translucent, and at least a portion of the other of the section of the cover plate and the section of the base plate is transparent, translucent, or reflective, and
 a) wherein an inner surface of the side wall of the well of one of the two, or more than two sample tabs has a height of a first value, and the inner surface of the side wall of the well of each of the other one, or more than one of the two, or more than two sample tabs has a height substantially equal to the first value, and
 wherein the bottom wall of the well of one of the two, or more than two sample tabs has a length of a second value, and the top surface of the bottom wall of the well of each of the other one, or more than one of the two, or more than two sample tabs has a length less than or greater than the second value, or b) wherein an inner surface of the side wall of the well of one of the two, or more than two sample tabs has a height of a first value, and the inner surface of the side wall of the well of each of the other one, or more than one of the two, or more than two sample tabs has a height less than or greater than the first value, and wherein the bottom wall of the well of one of the two, or more than two sample tabs has a length of a second value, and the top surface of the bottom wall of the well of each of the other one, or more than one of the two, or more than two sample tabs has a length substantially equal to the second value.

The present invention also provides the sample tab as described above, wherein at least a portion of the bottom wall of the well is transparent or translucent; and at least a portion of the section of the cover plate is transparent or translucent, and at least a portion of the section of the base plate is transparent or translucent; or at least a portion of the section of the cover plate is transparent or translucent, and at least a portion of the section of the base plate is reflective; or at least a portion of the section of the cover plate is reflective, and at least a portion of the section of the base plate is transparent or translucent.

The present invention also provides the sample tab as described above, wherein the bottom wall of the well is transparent or translucent; and the section of the cover plate is transparent or translucent, and the section of base plate is transparent or translucent, or the section of the cover plate is transparent or translucent, and the section of the base plate is reflective, or the section of the cover plate is reflective, and the section of the base plate is transparent or translucent.

The present invention also provides the sample tab as described above, wherein the bottom wall of the well is defined by the section of the base plate; and at least a portion of the section of the cover plate is transparent or translucent, and at least a portion of the section of the base plate is transparent or translucent; or at least a portion of the section of the cover plate is transparent or translucent, and at least a portion of the section of the base plate is reflective; or at least a portion of the section of the cover plate is reflective, and at least a portion of the section of the base plate is transparent or translucent.

The present invention also provides the sample tab as described above, wherein the bottom wall of the well is defined by the section of the base plate; and the section of the cover plate is transparent or translucent, and the section of base plate is transparent or translucent, or the section of the cover plate is transparent or translucent, and the section of the base plate is reflective, or the section of the cover plate is reflective, and the section of the base plate is transparent or translucent.

In another aspect, the present invention provides a sample tab comprising:

a base plate having a top surface and a bottom surface, the top surface of the base plate defining a first plane;

a well disposed on a section of the base plate, the well having a side wall and a bottom wall, the side wall and the bottom wall being defined by the base plate, wherein a top surface of the bottom wall defines a second plane, the second plane disposed above or below the first plane, and a cover plate hingedly connected to the base plate, the cover plate having an open position allowing a sample to be introduced into the well and a closed position in which a bottom surface of a section of the cover plate covers the well, wherein at least a portion of one of the section of the cover plate and the section of the base plate is transparent or translucent, and at least a portion of the other of the section of the cover plate and the section of the base plate is transparent, translucent or reflective.

In a further aspect, the present invention provides a sample tab comprising:

a base plate having a top surface, a bottom surface, and an opening extending from the top surface to the bottom surface, the top surface of the base plate defining a first plane, and the bottom surface of the base plate defining a second plane;

an insert comprising a well for insertion within the opening, the well having a side wall and a bottom wall, the insert disposed at least partly in the opening, wherein a top surface of the bottom wall defines a third plane, the third plane being above the first plane, coincident with the first plane, between the first and the second plane, coincident with the second plane, or below the second plane, and a cover plate connected to the base plate, the cover plate having an open position allowing a sample to be introduced in the well and a closed position in which a bottom surface of a section of the cover plate covers the well, wherein at a least a portion of one of the section of the cover plate and the bottom wall of the well is transparent or translucent, and at least a portion of the other of the section of the cover plate and the bottom wall of the well is transparent, translucent or reflective.

The present invention also provides a set or combination of two, or more than two sample tabs, wherein each of the two, or more than two sample tabs comprises:

a base plate having a top surface, a bottom surface, and an opening extending from the top surface to the bottom surface, the top surface of the base plate defining a first plane, and the bottom surface of the base plate defining a second plane;

an insert comprising a well for insertion within the opening, the well having a side wall and a bottom wall, the insert disposed at least partly in the opening, wherein a top surface of the bottom wall defines a third plane, the third plane being above the first plane, coincident with the first plane, between the first and the second plane, coincident with the second plane, or below the second plane, and a cover plate connected to the base plate, the cover plate having an open position allowing a sample to be introduced in the well and a closed position in which a bottom surface of a section of the cover plate covers the well, wherein at a least a portion of one of the section of the cover plate and the bottom wall of the well is transparent or translucent, and at least a portion of the other of the section of the cover plate and the bottom wall of the well is transparent, translucent or reflective, and a) wherein an inner surface of the side wall of the well of one of the two, or more than two sample tabs has a height of a first value, and the inner surface of the side wall of the well of each of the other one, or more than one of the two, or more than two sample tabs has a height substantially equal to the first value, and wherein the top surface of the bottom wall of the well of one of the two, or more than two sample tabs has a length of a second value, and the top surface of the bottom wall of the well of each of the other one, or more than one of the two, or more than two sample tabs has a length less than or greater than the second value, or b) wherein an inner surface of the side wall of the well of one of the two, or more than two sample tabs has a height of a first value, and the inner surface of the side wall of the well of each of the other one, or more than one of the two, or more than two sample tabs has a height less than or greater than the first value, and wherein the top surface of the bottom wall of the well of one of the two, or more than two sample tabs has a length of a second value, and the top surface of the bottom wall of the well of each of the other one, or more than one of the two, or more than two sample tabs has a length substantially equal to the second value.

The present invention also relates to the sample tab as described above, wherein at least a portion of the section of the cover plate is transparent or translucent, and at least a portion of the bottom wall of the well is transparent or translucent; or at least a portion of the section of the cover plate is transparent or translucent, and at least a portion of the bottom wall of the well is reflective; or at least a portion of the section of the cover plate is reflective, and at least a portion of the bottom wall of the well is transparent or translucent.

The present invention also provides the sample tab as described above, wherein the section of the cover plate is transparent or translucent, and the bottom wall of the well is transparent or translucent, or the section of the cover plate is transparent or translucent, and the bottom wall of the well is reflective, or the section of the cover plate is reflective, and the bottom wall of the well is transparent or translucent.

The present invention also provides the sample tab as described above wherein the side wall comprises one, or more than one overflow opening, and the side wall is surrounded by a containment wall, wherein the side wall and the containment wall define an overflow channel therebetween, for collecting excess sample as it is squeezed out by the closing cover plate.

The containment wall may comprise a sealing member on its upper surface. The sealing member may be an O ring, or a pliable material integral with the containment wall. In another example, the cover plate is attached to the tab so that the sample proximate the portion of the cover plate connected to the base plate makes contact with the cover plate first, and as the cover plate closes, excess sample is squeezed out through the one, or more than one overflow opening and into the overflow ring.

The cover plate may be connected to the base plate or may be separate. Further, the sample tab may comprise a locking member that associates with a corresponding mating member, thereby permitting the cover plate to be connected to the base plate. The locking member may comprise, but is not limited to, an element capable of frictionally engaging an outer portion of a containment wall, such as a circular ring, or one, or more than one clip capable of frictionally engaging and attaching the cover plate to the base plate. The locking members may be located on the base plate, cover plate or both the base plate, and the cover plate. Similarly, the associated mating member that receives the locking member may be located on the base plate, cover plate or both the base plate, and the cover plate.

In other examples of the above-defined sample tab, the side wall of the well is circular. In further examples, the containment wall is circular.

In another aspect, the present invention provides a method for analyzing a sample, comprising:

i) adding a sample into the well of the sample tab defined above;

ii) closing the cover plate of the sample tab;

iii) inserting the sample tab into an instrument for analyzing the sample, and iv) analyzing the sample.

In another aspect, the present invention provides a method for analyzing a set of two, or more than two samples, comprising:

i) adding one of the two, or more than two samples into the well of one of the two, or more than two sample tabs of the set described above;

ii) closing the cover plate of the sample tab from step i);

iii) inserting the sample tab from step ii) into an instrument for analyzing the sample added in step i);

iv) analyzing the sample, and v) repeating steps i)–iv) for each of the other one, or more than one sample tab of the two, or more than two sample tabs.

In an example of the above methods, in the step of inserting (step iii)), the sample tab is placed in a horizontal position within a sample holder of the instrument, and wherein the sample is analyzed by projecting electromagnetic radiation through the well in a direction substantially perpendicular to the position of the sample tab.

In another aspect, the present invention provides a sample tab comprising:

a base plate having a top surface and a bottom surface;

a well defined by a top surface of a section of the base plate and by a wall extending above the top surface of the base plate, wherein the wall extending above the top surface of the base plate comprises one, or more than one overflow opening, and is surrounded by a containment wall, and wherein the containment wall and the wall extending above the top surface of the base plate define an overflow channel therebetween, and a cover plate connected to the base plate, the cover plate having an open position allowing a sample to be introduced into the well and a closed position in which a bottom surface of a section of the cover plate covers the well, wherein at a least a portion of one of the section of the cover plate and the section of the base plate is transparent or translucent, and at least a portion of the other of the section of the cover plate and the section of the base plate is transparent, translucent or reflective.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

This summary does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 3 depicts various aspects of an example of a sample tab of the present invention.

FIG. 4 depicts various aspects of an alternate example of a sample tab of the present invention.

FIG. 5 depicts various aspects of an alternate example of a sample tab of the present invention.

FIG. 7 shows cross sectional views of additional examples according to the present invention. FIG. 7A is a cross-sectional view in the direction of the arrows 7A—7A in FIG. 2. The cover plate connected to the base plate of the illustrated sample tab has been removed for the sake of clarity. FIG. 7B is a transverse cross-sectional view of an alternate example of the sample tab of the present invention. The cover plate connected to the base plate of the illustrated sample tab has been removed for the sake of clarity.

FIG. 8 shows transverse cross-sectional views through the sample well of further examples of sample tabs according to the present invention. In FIGS. 8A–D, the cover plates connected to the base plate of the illustrated sample tabs have been removed for the sake of clarity. The side wells of the sample tabs of FIGS. 8B and 8D include one, or more than one opening leading to the containment channel, which are not shown in these Figures.

FIG. 9 shows transverse cross-sectional views through the sample well of further examples of sample tabs according to the present invention. In FIGS. 9A–D, the cover plates connected to the base plate of the illustrated sample tabs have been removed for the sake of clarity. The side wells of the sample tabs of FIGS. 9B and 9D include one, or more than one opening leading to the containment channel, which are not shown in these Figures.

FIG. 10 shows transverse cross-sectional views through the sample well of further examples of sample tabs according to the present invention. In FIGS. 10A–D, the cover plates connected to the base plate of the illustrated sample tabs have been removed for the sake of clarity. The side wells of the sample tabs of FIGS. 10B and 10D include one, or more than one opening leading to the containment channel, which are not shown in these Figures.

FIG. 11 shows a transverse cross-sectional view through an additional example of a sample tab according to the present invention. The cover plate connected to the base plate of the illustrated sample tab has been removed for clarity.

FIG. 12 shows transverse cross-sectional views through the sample well of examples of sample tabs according to the present invention. FIGS. 12A–C show different volumes of the sample well obtained by varying the diameter of a bottom wall that is coplanar with the top surface of the base plate. The cover plates connected to the base plate of the illustrated sample tabs have been removed for the sake of clarity.

FIG. 13 shows transverse cross-sectional views through the sample well of examples of sample tabs according to the present invention. FIG. 13A–C show different volumes of the sample well obtained by varying the diameter of a bottom wall that lies below the plane of the top surface of the base plate. The cover plates connected to the base plate of the illustrated sample tabs have been removed for the sake of clarity.

FIG. 14 shows transverse cross-sectional views through the sample well of examples of sample tabs according to the present invention. FIG. 14A–C show different volumes of the sample well obtained by varying the diameter of the bottom wall that lies above the plane of the top surface of the base plate. The cover plates connected to the base plate of the illustrated sample tabs have been removed for the sake of clarity.

FIG. 15 shows a transverse cross-sectional view through examples of the disposable sample well according to the present invention. FIGS. 15A–C show different volumes of the sample well obtained by varying the diameter of a bottom wall of an insert that may be fitted within a base plate.

FIG. 16 shows a transverse cross-sectional view through examples of the disposable sample well according to the present invention. FIGS. 16A–C show different volumes of the sample well obtained by varying the diameter of a bottom wall of an insert that may be fitted within a base plate.

FIG. 17 shows examples of transverse cross-sectional views of the disposable sample well according to the present invention. FIG. 17A–C show different volumes of the sample well obtained by varying the diameter of a bottom wall of an insert that may be fitted within a base plate.

FIG. 18 shows a transverse cross-sectional view of another example of a disposable well or insert according to the present invention, which contains an overflow channel.

FIG. 19 shows a transverse cross-sectional view of an additional example of an insert fitted within a sample tab according to the present invention.

FIG. 20 shows a transverse cross-sectional view of an additional example of an insert fitted within a sample tab according to the present invention.

DESCRIPTION OF PREFERRED EMBODIMENT

Figure 1:
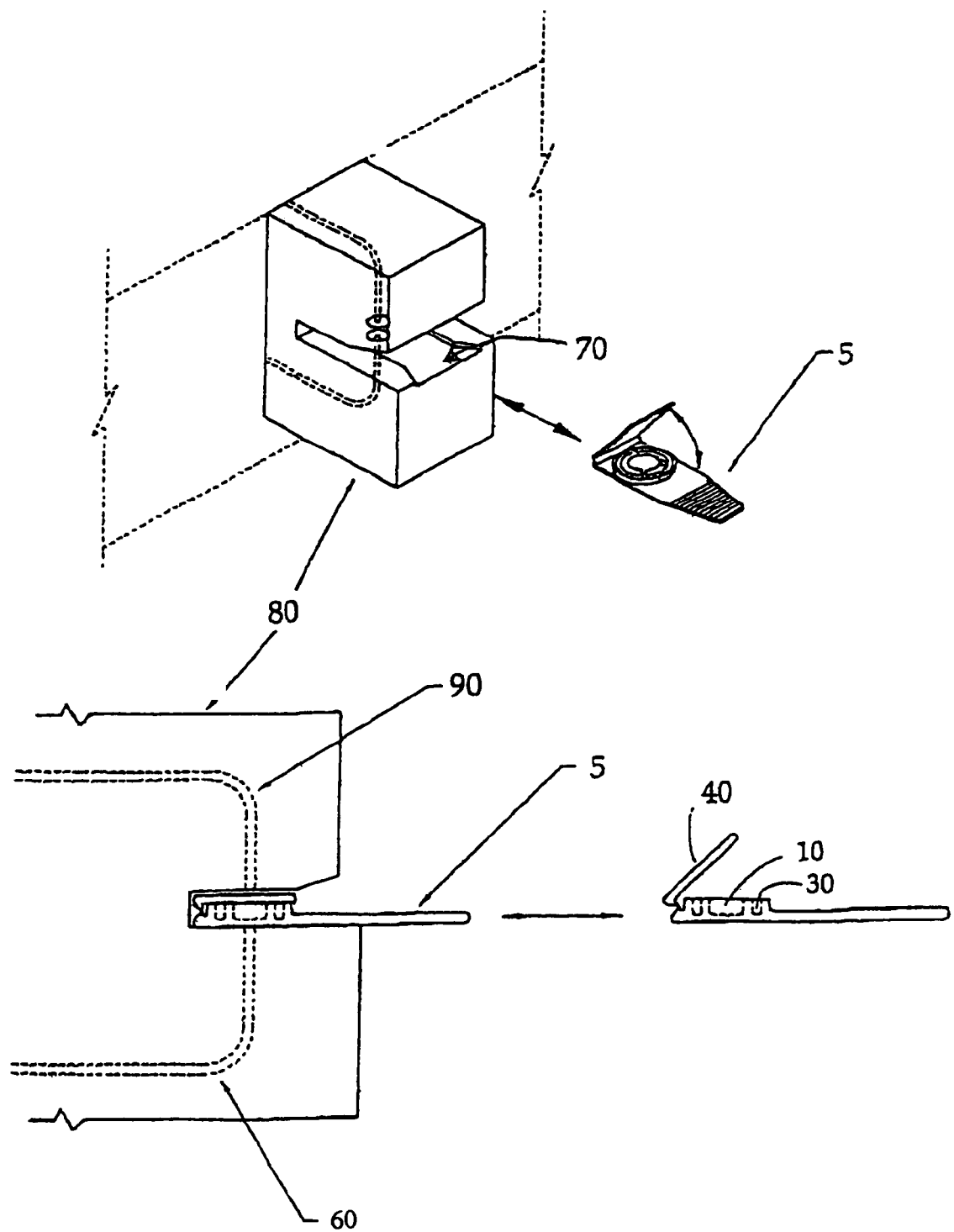
FIG. 1 is a perspective view of a system incorporating an apparatus of the present invention for measuring Hemoglobin $A_{1c}$.

The invention relates to a tab for retaining a sample for analysis. More particularly, the present invention provides a sample tab and a method for sample analysis using a variety of instruments including a spectrophotometer or a microscope.

The following description is of a preferred embodiment by way of example only and without limitation to the combination of features necessary for carrying the invention into effect.

The present invention provides a sample tab that may be used for the determination of a substance within a sample using spectroscopic or microscopic analysis. The sample tab comprising a base plate, a well disposed on the base plate and a cover plate. In a broad aspect, the present invention also provides an apparatus for determining the concentration of a substance in a sample where the apparatus comprises a sample housing for receiving a sample tab; a radiation source; and radiation detector, operatively coupled with a system for providing a determination of the substance within the sample based on the determination of transmitted or reflected radiation.

According to one embodiment of the present invention, the sample housing comprises a block with a slit for inserting the sample tab. The sample tab consists of a base plate with a well on the base plate for containing the sample and a cover plate which can be placed over the well prior to inserting the sample tab in the housing, preferably the cover plate closes automatically when inserted in the sample housing. The well may be of any desired shape and of any suitable volume.

The present invention also provides a method of determining the concentration of a substance within a sample using a sample tab.

For example, which is not to be considered limiting in any manner, the sample tab as described herein may be used to determine the occurrence or concentration of any substance within a biological or non-biological sample. Preferably the sample is a fluid sample, for example but not limited to blood, or a semi-solid sample. A non-limiting example is provided herein where the sample tab of the present invention may be used, in combination with a spectrophotometer, to test a diabetic patient's compliance with their insulin dosing regime by quantifying The amount of $HbA_{1c}$ and Hb contained in a blood specimen taken from the patient, without further treatment of the specimen, and comparing the concentration of $HbA_{1c}$ and Hb within the sample. In this non-limiting example, an elevated ratio of $HbA_{1c}$ reflects a lack of patient compliance. However, it is to be understood that the sample tab of the present invention may be used to determine the concentration of any substance within a sample using spectroscopic, microscopic, or other analysis that requires that a sample be retained within a translucent or transparent tab. Furthermore, the sample tab as described herein may comprise at least one surface that reflects incident radiation. Examples of other biological samples that may be determined include, but are not limited to whole blood, plasma, serum, sinovial fluid, cerebral spinal fluid, urine, lymph, mucus, faeces, and semen. However, non-biological samples may also be readily tested as described herein. Examples of non-biological samples include, but are not limited to dairy products, for example, milk, cheese, cottage cheese, yoghurt, or ice cream, or beverages, or semi-solid foods. Non-limiting examples of substances that may detected in these samples include Hemoglobin, one or more proteins, albumin, globulin, fat, lactose etc. An example of a non-limiting measurement that can be made is hematocrit in blood.

According to the present invention, there is provided a method of quantification of one or more substances within a sample comprises the steps of:

i) generating a calibration algorithm for each of the substances to be determined;

ii) obtaining a sample and placing the sample into a sample tab;

iii) measuring with a spectrophotometer, absorbance of radiation by each of the substances in the sample; and iv) incorporating the absorbance measured in step (iii) in the algorithms generated in (i), and calculating the concentration of the substances in the sample.

For example which is not to be considered limiting, if the sample is blood, then the concentration of $HbA_{1c}$ and Hb may be determined. In this case the method of quantification of the one or more chemical compounds comprises the steps of:

i) generating a calibration algorithm for each of the $HbA_{1c}$ and Hb;

ii) obtaining a blood sample and placing the blood sample into a sample tab, iii) measuring with the spectrophotometer, absorbance of radiation by each of the $HbA_{1c}$, and Hb in the blood sample; and iv) incorporating the absorbance measured in step (iii) in the algorithms generated in (i), and calculating the concentration of the $HbA_{1c}$ and Hb in the sample. Alternatively, one algorithm can be developed for the ratio of $HbA_{1c}$, to Hb expressed as % $HbA_{1c}$.

According to a method of the present invention quantification includes calculation of the first derivatives of at least two portions of a spectrum generated from a scan for each of the chemical compounds being determined, for example but not limited to, $HbA_{1c}$, and Hb which may then be used to calculate each of the $HbA_{1c}$ and Hb concentrations in the sample. Similarly, PLS (Partial Least Squares) or PCA (Principal Components Analysis) may be used depending on the analyte being analysed.

According to another aspect of the present invention, the method as described herein can be used with reflectance instead of absorbance. In the case of reflectance, either the base plate or the cover plate may have a reflective surface or may be made of reflective material. Such a reflective surface or material could include any suitable reflective coating, for example, but not limited to, a ceramic coating, barium sulfate, Spectralon™, Spectraflect™, or Duraflect™.

Turning now to the sample housing within a spectrophotometer and sample tab, as may be seen in FIG. 1, electromagnetic radiation from the spectrophotometer is delivered to the sample in the sample tab (5) through a source or incident optical fibre (60) while the sample rests in a sample tab holder (70) within a sample housing (80). The electromagnetic radiation passing through the sample tab and specimen is received by a receiving optical fiber (90), and processed further to determine concentrations of one or more substances within the sample.

The instrument shown in FIG. 1 is configured for the use of a horizontal sample tab, however the sample tab may also be used in a vertical position within a spectrophotometer or other apparatus. For example, the sample tab may be inserted within a cuvette holder for use within standard spectrophotometers. In this application, the cuvette holder would be configured to hold the sample tab within the path of the radiation beam, as would be the case with a standard cuvette. The cuvette holder can be configured for horizontal or vertical use. However, there are several advantages that may be associated with horizontal use. For example, in sample comprising particulate matter, by maintaining the sample tab horizontally there is a uniform settling of components within the sample, in the direction of the incident radiation beam, such that the particulate matter remains in the light path even after it has travelled. An example of particulate matter is red blood cells in a blood sample.

Sample Tab

According to an aspect of the present invention, there is provided a sample tab for retaining a sample for further analysis, for example, but not limited to using a spectrophotometer or a microscope. A non-limiting example for the use of the sample tab of the present invention is to monitor a diabetic patient's compliance with their insulin dosing regime by spectrophotometry.

The sample tab (5) comprises:

a) a base plate (45) with a top surface (48) and a bottom surface, the top surface (48) of the base plate defining a first plane (70), the base plate characterized as having at least a portion that permits transmission or reflectance of electromagnetic radiation;

b) a well or sample cavity (10) disposed on a section of the base plate for retaining the sample, the well having a side wall (15) and a bottom wall (13), wherein a top surface (12) of the bottom wall (13) defines a second plane (75), the second plane being coincident with the first plane, disposed above the first plane, or disposed below the first plane. For example, the second plane may be parallel to and offset from the first plane. More particularly, the top surface of the base plate and the top surface of the bottom wall of the well define a first horizontal plane, and a second horizontal pane, respectively, wherein the second horizontal plane is coincident with or may be vertically offset from the first horizontal plane. The well may be of any desired volume and may be of any shape; and c) a cover plate (40) having at least a portion that permits transmission or reflectance of electromagnetic radiation.

Examples of the above-defined sample tabs are shown in FIGS. 7B, 8A, 8C, 9A, 9C, 10A, and 10C.

The sample tabs of the present invention may also optionally comprise one, or more than one overflow groove or opening (20) in the side wall (15) of the well (10) permitting drainage of excess sample from within the well. Examples of such sample tabs are shown in FIGS. 2–6, 7A, 8B, 8D, 9B, 9D, 10B and 10D.

In use, a sample is retained in the well between the base plate and the cover plate so that electromagnetic radiation may pass through the base plate, through a sample in the well, and the cover plate. However, it is within the scope of the present invention that the radiation beam may travel through the sample, and be reflected off either the base plate or cover plate thereby doubling the path length of the radiation beam. By doubling the path length, a reduced volume of sample may be used during analysis. Either the base plate or the cover plate may have a reflective surface, or may be made of, reflective material.

The sample well defined by a side wall and a bottom wall may contain one, or more than one opening or groove within the side wall, and an overflow channel for collecting excess sample as it is squeezed out by the closing cover plate. Preferably, the side wall contains one, or more than one opening, and an overflow channel, and the cover plate is connected to the base plate by, for example, a hinge or a tether, so that the sample proximate the edge of the cover plate connected to the base plate, makes contact with the cover plate first and as the cover plate closes, excess sample is squeezed out through the one, or more than one opening, which are preferably situated at the side where the cover plate makes final contact with the rest of the tab, and into the overflow channel. If the cover plate is connected to the base plate by way of a hinge, this design can help the sample tab slide into the receptor of an instrument, such as a spectrophotometer.

Figure 2:
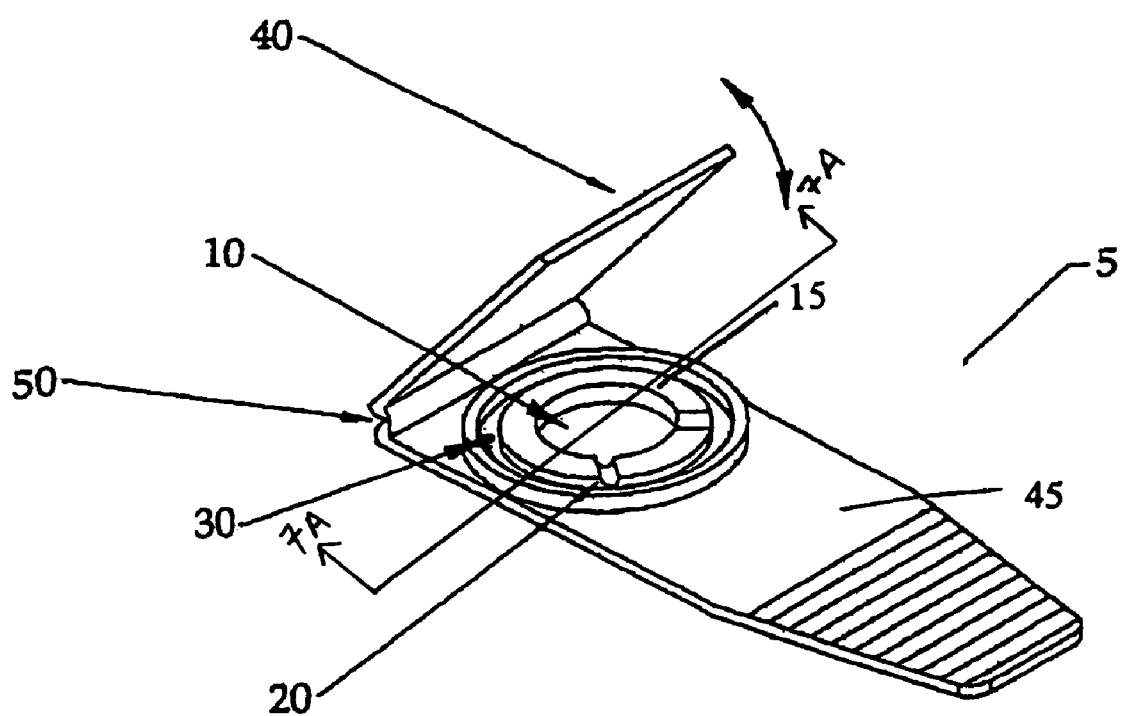
FIG. 2 is a perspective view illustrating the sample tab of the apparatus of FIG. 1.

Referring now to FIG. 2, there is shown an aspect of an embodiment of the sample tab of the present invention. Shown in FIG. 2, is sample tab (5) comprising base plate (45), cover plate (40) and sample well (10) defined by wall (15). Sample well (10) may be of any volume required, for example, but not limited to, a size sufficient to allow a drop of blood to fill the well, preferably with some excess. For example, the volume of the sample well may be from about 10 μL to about 10 mL, or an amount or subrange therebetween, from about 50 μL to about 5 mL, or an amount or subrange therebetween, from about 100 μL to about 2.5 mL, or an amount or subrange therebetween, from about 250 μL to about 1 mL, or an amount or subrange therebetween, or from about 500 μL to about 1 mL, or an amount or subrange therebetween.

The sample well may also be large enough to accommodate about 10 mL of a sample, for example urine or a beverage. It must be understood that these are just non-limiting examples of sample sizes. In an embodiment which is not meant to be considered limiting in any manner, the well is circular and comprises dimensions of about 4 mm in diameter and about 2 mm in depth. Overflow openings or grooves (20) in wall (15) allow excess sample to flow out of sample well (10) when cover plate (40) is closed over sample well (10) and base plate (45). The height of the side wall (15) of the well may vary depending on the sample volume desired, but, generally does not exceed the height of the containment wall (37).

A second wall, such as, but not limited to, a containment wall (37) may be employed to retain the sample that overflows sample well (10), into an overflow channel (30) to prevent leakage of fluid from the sample tab, while permitting a sample of sufficient volume to fill the well. In this regard, the vertical height of containment wall (37) is less than or equal to the height of closed wall (15) defining sample well (10), more preferably it is equal to the height of closed wall (15) defining sample well (10). Cover plate (40) is preferably attached to base plate (45) by hinge (50) or other suitable attachment means known in the art. However, a non-hinged cover plate may also be used. The cover plate may be snapped on to the base plate as described below.

The cover plate, the base plate, or the entire sample tab may be manufactured from any suitable material known in the art for example, but not limited to, a transparent, translucent material, such as glass, plastic or a combination thereof, or a reflective material. If the base plate and cover plate are transparent or translucent, then it is preferred that the base plate, and cover plate comprise a transparent or translucent plastic, such as but not limited to polypropylene, polycarbonate, polyethylene, or polystyrene, however, a glass plate may also be used. If either of the base plate or cover plate is reflective, then a reflective material, for example but not limited to a ceramic coating, barium sulfate, Spectralon™, Spectraflect™, or Duraflect™ may be used for one of the base or cover plates. As described in more detail below, the sample tab may be fitted with an insert (e.g. see 11; FIGS. 11, 15–19 and 20) that comprise the sample well. In this case, the sample tab may be opaque and of a different material that used for the insert, for example but not limited to a plastic, pliable polymer, nylon or similar material.

Optionally, the sample tab of the present invention may comprise a locking member to lock cover plate (40) to the base plate (45). The locking member may comprise a portion of the cover plate, base plate or both. Further, the locking member may reversibly or irreversibly lock the cover to the base plate. Any locking member known in the art may be employed with the sample tab of the present invention, for example, but not limited to those as shown in FIG. 3–5. The use of a containment wall ensures that the sample is retained within the sample tab and reduces contamination between samples. Furthermore, by locking the cover plate of the sample tab in a closed position, the sample tab may be readily disposed of after use without sample leakage, or the sample tab may be used in a vertical position, for example within a cuvette holder adapted for use within spectrophotometers.

Figure 3A:
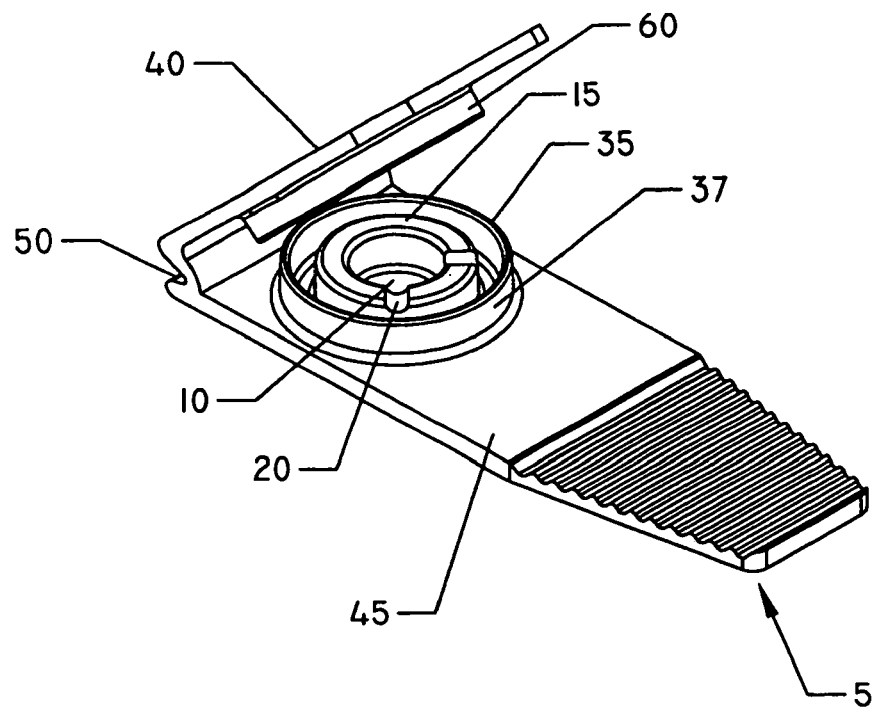
FIG. 3A illustrates an oblique view of the sample tab.
Figure 3B:
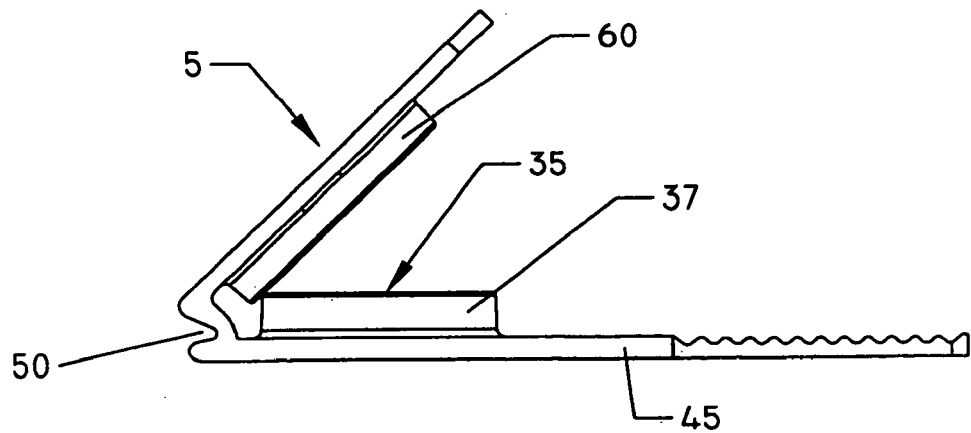
FIG. 3B exhibits a side view of the sample tab.

Referring now to FIG. 3, there is shown an alternate aspect of an embodiment of the present invention. In FIG. 3A, there is shown a perspective view of a sample tab (5) with cover plate (40) positioned over base plate (45) and revealing a well (10) defined by wall (15), overflow grooves (20), overflow-channel (30; FIGS. 1 and 2), and hinge (50). FIG. 3B shows a side view of a sample tab (5) wherein cover plate (40) is open. Also shown in FIG. 3B is a locking member (60) which permits cover plate (40) to be fastened to base plate (45). In the aspect of the embodiment shown in FIG. 3B, the locking member (60) comprises a circular ring, capable of frictionally engaging containment wall (37), thereby reversibly attaching cover plate (40) to base plate (45), preventing the escape of a sample from the sample tab. However, as would be evident to someone of skill in the art, the locking member (60) comprising a circular ring may be attached to the base plate (45) in a variety of ways, for example, but not limited to, frictionally engaging a protrusion located on the outside of containment wall (37), or frictionally engaging a recessed groove in the base plate (38; FIGS. 8B, 8D), adjacent to and below containment wall (37).

When the cover plate is closed over the well, and attached to the base plate, it is preferred that the top surface (35) of the containment wall (37) seals against the lower surface of the cover slip. However, the locking member (60) may also be used to help seal the sample within the sample tab should any leakage occur past the containment wall (37). The embodiment shown in FIG. 3 shows a hinged cover plate, however, it is to be understood that cover plate (40) comprising locking member (60) may be separate from base plate (45), and the cover plate may be attached to the base plate after a sample is introduced into well (10). Since the cover plate is attached to the base plate, the final sample tab assembly serves as one unit.

If it is required that the sample be effectively sealed within well (10), then the upper surface of containment wall (37) may be modified to comprise a sealing member (35), for example an "O ring" that fits within a grooved upper surface of the containment wall, the top surface of the containment wall (37) may be made of a softer pliable material, for example silicon, yet integral with the base plate. Alternatively, the top surface (35) of the containment wall (37) may be lubricated so that when cover slip (40) is attached to base plate (45) a seal is formed between base plate (45) and cover slip (40). The use of a containment wall ensures that the sample is retained within the sample tab and reduces contamination between samples. Furthermore, by locking the cover plate of the sample tab in a closed position, the sample tab may be readily disposed of after use without sample leakage.

Figure 4A:
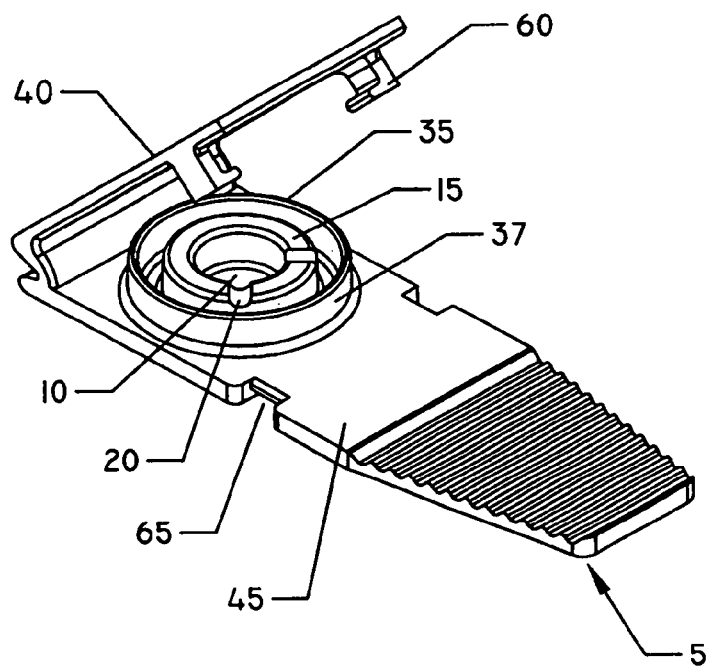
FIG. 4A illustrates an oblique view of the sample tab.
Figure 4B:
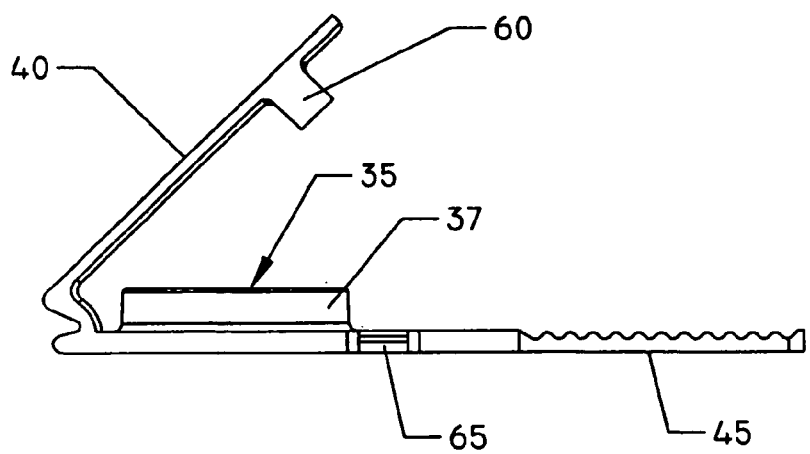
FIG. 4B exhibits a side view of the sample tab.

Referring now to FIG. 4, there is shown an alternate aspect of an embodiment of the present invention. FIG. 4A shows a perspective view, and in FIG. 4B, a side view, of a sample tab (5) with cover plate (40) and base plate (45). In these figures, cover plate (40) is open revealing well (10) defined by wall (15), overflow grooves (20), and containment wall (37). Also shown in FIG. 4B are locking members (60) which permit cover plate (40) to be attached to base plate (45). In the aspect of the embodiment shown in FIGS. 4A and 4B, locking members (60) comprise one or more clips capable of frictionally engaging base plate (45), at a corresponding recess (65) within the base plate, thereby locking cover plate (40) to base plate (45) and preventing the escape of a sample from well (10). Locking members (60) may be positioned so that when engaged with the base plate at the corresponding recess (65), they do not extend below the lower surface of the base plate, so that a smooth bottom surface is obtained. Such a smooth surface may be required for sliding the sample tab into a receptor of an apparatus, or for microscopic viewing.

If it is required that the sample be effectively sealed within well (10), then the upper surface of containment wall (37) may be modified to comprise a sealing member (35), for example an "O ring" that fits within a grooved upper surface of the containment wall, the top surface of the containment wall (37) may be made of a softer pliable material, for example silicon, yet integral with the base plate. Alternatively, the top surface (35) of the containment wall (37) may be lubricated so that when cover slip (40) is attached to base plate (45) a seal is formed between base plate (45) and cover slip (40). As described above, the use of a containment wall and optionally a locking cover plate ensures that sample leakage is kept to a minimum.

Figure 5A:
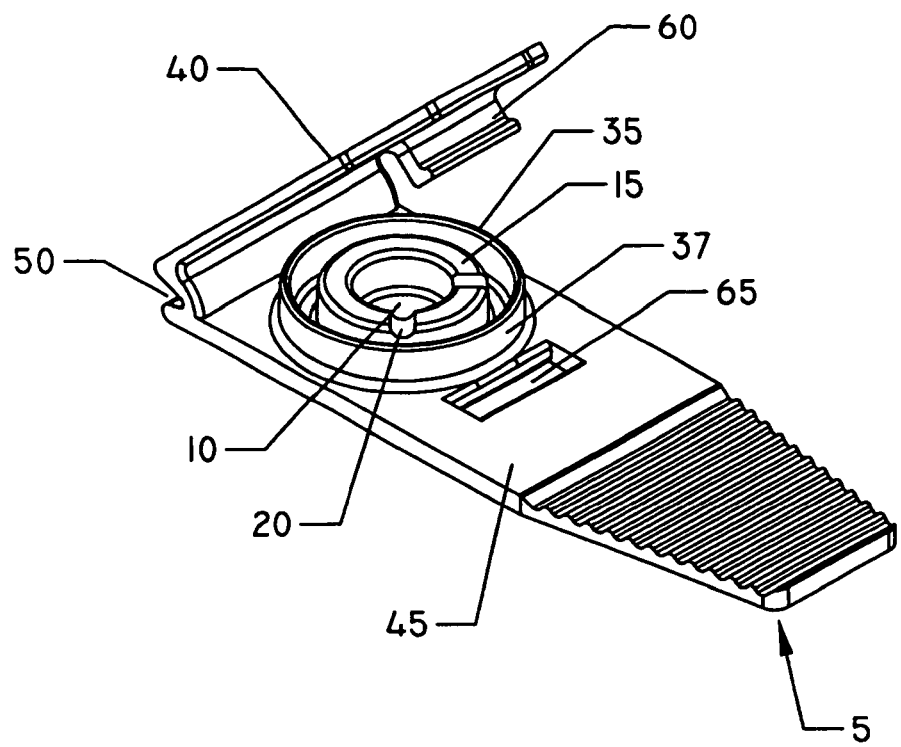
FIG. 5A illustrates an oblique view of the sample tab.
Figure 5B:
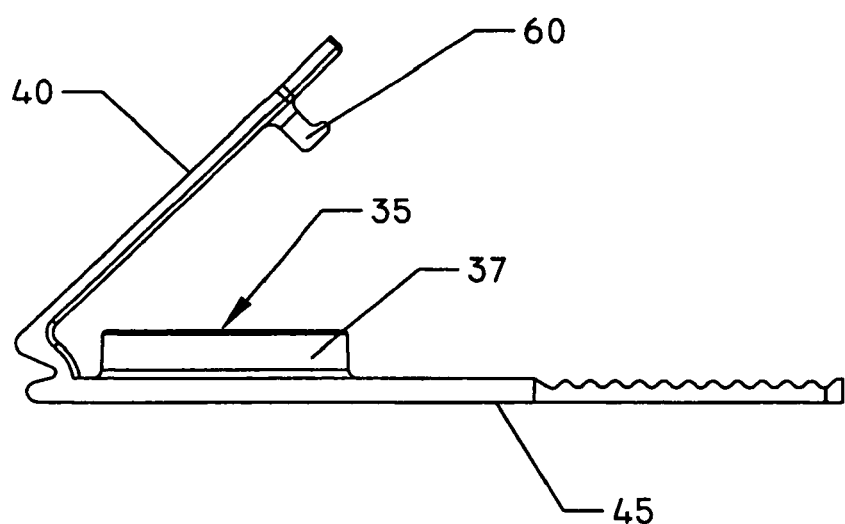
FIG. 5B exhibits a side view of the sample tab.
Figure 6:
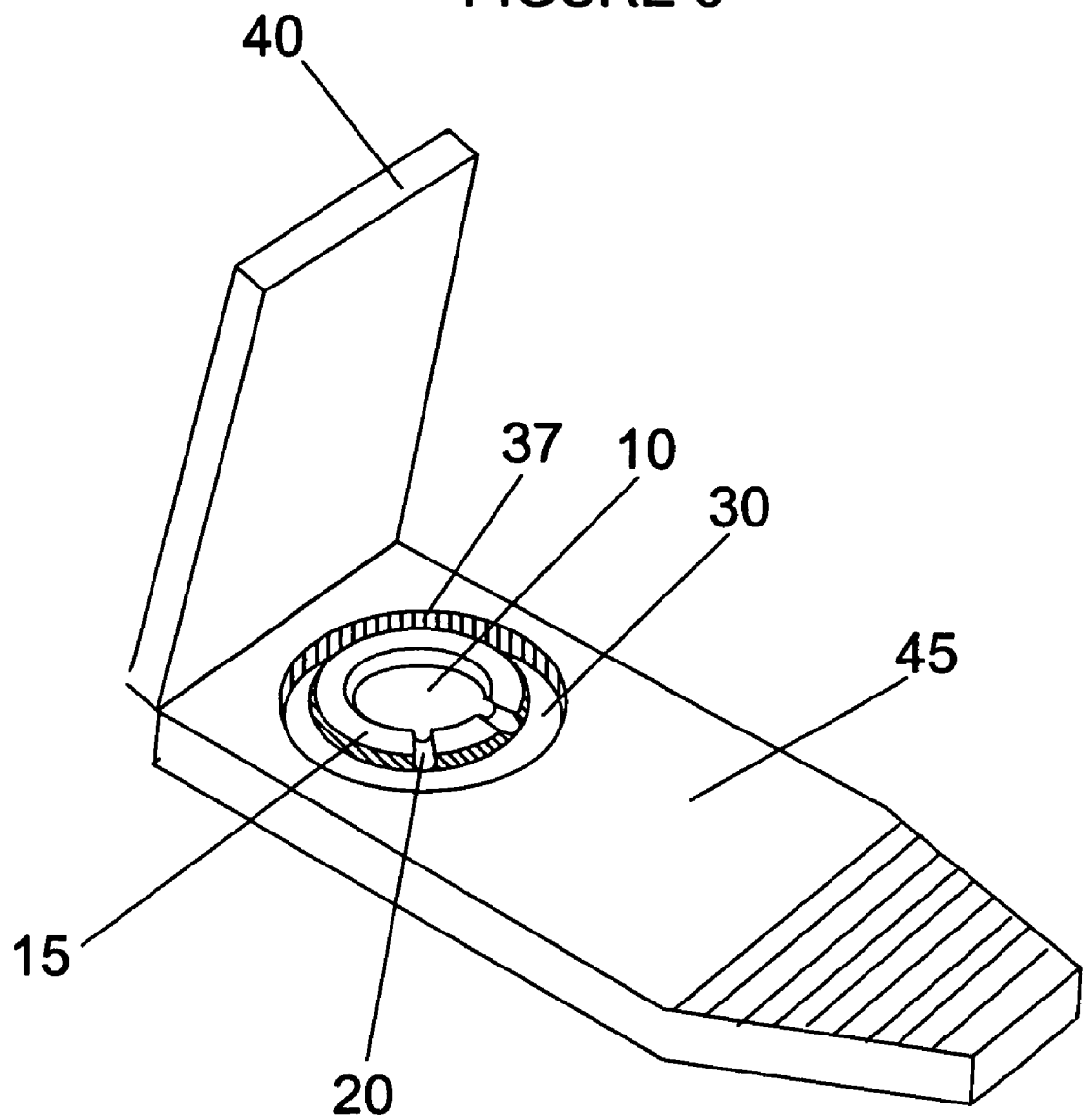
FIG. 6 is a perspective view of another example of a sample tab according to the present invention.

Referring now to FIG. 5, there is shown another aspect of embodiment of the present invention. In FIG. 5A, there is shown a perspective view, and in FIG. 5B a side view, of sample tab (5) with cover plate (40) positioned over base plate (45). In FIG. 5A, cover plate (40) is open revealing well (10) defined by wall (15), overflow grooves (20), containment wall (37) and hinge (50). Also shown in FIG. 5B is locking member (60) which permits cover plate (40) to be attached to base plate (45) by association with a corresponding mating recess (65) positioned on the base plate. In the aspect of the embodiment shown in FIGS. 5A and 5B, locking member (60) comprises a clip capable of frictionally engaging mating recess (65) and locking cover plate (40) to base plate (45), preventing the escape of the sample. The mating recess may extend through the base plate (45), and engage the bottom surface of the base plate, or the locking member may engage a snap portion within recess (65) and not extend thorough the base plate. A smooth bottom surface may be required for sliding the sample tab into a receptor of an apparatus, or for microscopic viewing. It is to be understood that the locking member (60) may be positioned in the base plate, and recess (65) positioned on the cover slip if desired.

If it is required that the sample be effectively sealed within well (10), then the upper surface of containment wall (37) may be modified to comprise a sealing member (35) so that when cover slip (40) is attached to base plate (45) a seal is formed between base plate (45) and cover slip (40). In this embodiment, the use of a containment wall ensures that the sample is retained within the sample tab and reduces contamination between samples. Furthermore, by locking the cover plate of the sample tab in a closed position, the sample tab may be readily disposed of after use without sample leakage, or it may be used in a vertical position as required.

FIGS. 3–5 illustrate a locking member (60) on the cover plate (40) of the sample tab (5) of the present invention. However, it is also possible that locking member (60) may comprise a portion of base plate (45), and that the corresponding recess (65) be positioned on the cover plate (40).

In the examples of the sample tab shown in FIGS. 2–6 and 7A–B, a top surface (48) of the base plate (45) and a top surface (12) of the well (10) disposed on the base plate (45) define a first plane (70) and a second plane (75), respectively, which are coincident. In other examples, the top surface (48) of the base plate (45) and the top surface (12) of the bottom wall (13) of the well (10, 11) define a first plane (70) and a second plane (75), respectively, wherein the second plane is disposed below the first plane, as illustrated, for example, in FIGS. 8A–D and 9A–D, or the second plane is disposed above the first plane, as shown, for example, in FIGS. 10A–D.

The side and bottom walls of the well may be defined by the base plate, that is, the base plate and the well may be formed as a single structure, by, for example, injection molding (see 10 in FIGS. 7A–B, 8A–B, 9A–B and 10A–B). In other examples, the well is a separate structure, or insert, having side and bottom walls, which is fixedly or removably connected to a separately formed base plate, as illustrated by 11 in FIGS. 8C–D, 9C–D, 10C–D, and 11. For example the insert (11) may be press fit within an opening of appropriate size and shape that is defined by the base plate (45).

The top surface of the side wall of the well (10) disposed on the sample tab may be level with the top surface (48) of the base plate (45; see FIGS. 8A–D), or extend above the top surface (48) of the base plate (45; see FIGS. 7A–B, 9A–D and 10A–D). Similarly, the top surface of the containment wall (37), when present, may be level with the top surface (48) of the base plate (45; FIGS. 8B, 8D), or above the top surface (48) of the base plate (35; FIGS. 7A, 9B, 9D, 10B and 10D). If the plane defined by the top surface (12) of the bottom wall (13) of the well (10), 75, is lower than the plane defined by the top surface (48) of the base plate (45), the base plate may contain a groove (38) for frictionally engaging a locking member connected to the cover plate (see FIGS. 8B and 8D).

In another example, illustrated in FIG. 11, the base plate (45) has a top surface (48), a bottom surface (52), and an opening extending from the top surface to the bottom surface, wherein the top surface of the base plate defines a first plane (80), and the bottom surface of the base plate defines a second plane (85). An insert (11) comprising a well (10) having a side wall (15) and a bottom wall (13) is disposed at least partly in the opening, wherein a top surface (12) of the bottom wall (13) defines a third plane (91), the third plane being above the first plane, coincident with the first plane, between the first and the second plane, coincident with the second plane, or below the second plane. In this example, the side wall of the well may be defined by the base plate, or the well may be fabricated as a separate structure. In the latter case, the well may be advantageously disposed of after use, and the base plate of the sample tab reused with a new well. Furthermore, a number of disposable sample wells of different volumes could be employed in this last example, permitting the analysis of a diverse array of samples of different volumes.

The insert (11) comprising well (10) may also define a containment channel (30) between the side wall (15) and a containment wall (37), as illustrated in FIG. 18, which are connected by one, or more than one overflow openings (not shown).

The insert (11) may be retained within the opening of the base plate (45) by frictional engaging the surface of the base plate defining the opening, as illustrated in FIG. 11. Alternatively, the insert (11) may be retained within the opening of the base plate (45) by use of a snap-fitting. For example, the insert (11) may contain a pair of ridges (92), which matingly engage with a corresponding pair of recesses or grooves (95) within the opening, as illustrated in FIG. 19, or alternatively, the opening may comprises a pair of ridges that matingly engage within a pair of recesses formed on the periphery of the well. In another example shown in FIG. 20, the insert (11) may comprising a flange (100) at or adjacent to its top surface, which has an outside diameter larger than the diameter of the opening of the base plate (45), so that the upper part of the well may rest above the upper part of the opening of the sample tab.

The insert (11) may be manufactured from any suitable material known in the art for example, but not limited to, a transparent, translucent material, such as glass, plastic or a combination thereof, or a reflective material. Examples of a transparent or translucent material include a transparent or translucent plastic, such as, but not limited to polypropylene, polycarbonate, polyethylene, or polystyrene, however, a glass plate may also be used. Examples of reflective materials, include, for example, but are not limited to a ceramic coating, barium sulfate, Spectralon™, Spectraflect™, or Duraflect™. As described above, a sample tab that is to be fitted with an insert (11) may be made from an opaque material that is the same or different from that used for the insert. For example which is not to be considered limiting in any manner, the sample tab may be made of a medium to soft plastic, pliable polymer, nylon or similar material. Such a material will permit the sample tab to remove and replace different inserts as required.

In addition, the section of the cover plate that contacts the top surface of the well when the cover plate is placed in the closed position, may be a separate component fabricated of a translucent, transparent or reflective material.

The depth or height of the inner surface of the side wall of the well (see "h"; FIGS. 12–17), and, therefore, the volume of the well (10) and the containment channel (30) may be varied according to the needs of the sample tab. For example, a shallow well and containment channel may be used when small samples are being tested using the sample tab. In addition, the combined height of the base plate, including the well, and any containment wall should not exceed a predetermined value A (e.g. see FIGS. 8A–D), so that when the cover plate is closed over the sample tab, the combined height of the closed cover plate and the base plate, will not exceed the height or clearance of a sample tab receptacle within a spectrometer that is used for measuring the values, for example, a concentration of an analyte within a sample placed within the well of the sample tab.

FIGS. 12A–C show additional examples of sample tabs according to the present invention, in which the top surface of the base plate defines a first plane (70) and the top surface (12) of the bottom wall (13) of the well (10) defines a second plane, wherein the first and the second planes are coincident. The volume of the well may be adjusted by increasing, or, alternatively, by decreasing the diameter (d) of the well, as shown in FIGS. 12B and 12C.

In addition, the volume of the well may be decreased or increased by shortening or lengthening, respectively, the height of the inner surface of the side wall of the well ("h", see FIGS. 12–14). For accommodating samples of increasingly smaller volumes, for example, samples in the range of from about 5 μL to 100 μL, sample tabs according to the present invention, in which the second plane (75) is disposed above the first plane (70), as illustrated, for example, in FIG. 14A, may be used. For samples of relatively larger volumes, for example, samples in the range of from about 500 μL to about 1 mL, sample tabs according to the present invention, in which the second plane (75) is disposed below the first plane (70), as illustrated, for example, in FIG. 13A, may be used. The volume of the well of the sample tabs shown in FIGS. 13A and 14A may also be varied by increasing or decreasing the length of the top surface of the bottom wall (12), for example the diameter of a circular well ("d"; see FIGS. 12–14). For example, the volume of the sample tabs shown in FIGS. 13A and 14A may be reduced by decreasing the length of the top surface of the bottom wall (12) of the well, as illustrated in FIGS. 13B–C and 14B–C, respectively.

Accordingly, the present invention provides a set of two, or more than two sample tabs, wherein each of the two, or more than two sample tabs comprises:

a base plate having a top surface and a bottom surface, the top surface of the base plate defining a first plane;

a well disposed on a section of the base plate, the well having a side wall and a bottom wall, wherein a top surface of the bottom wall defines a second plane, the second plane disposed above the first plane, below the first plane, or coincident with the first plane, and a cover plate hingedly connected to the base plate, the cover plate having an open position allowing a sample to be introduced into the well and a closed position in which a bottom surface of a section of the cover plate covers the well, wherein at least a portion of the bottom wall of the well is transparent or translucent, and wherein at a least a portion of one of the section of the cover plate and the section of the base plate is transparent or translucent, and at least a portion of the other of the section of the cover plate and the section of the base plate is transparent, translucent or reflective, or wherein the bottom wall of the well is defined by the section of the base plate, and wherein at least a portion of one of the section of the cover plate and the section of the base plate is transparent or translucent, and the other of the section of the cover plate and the section of the base plate is transparent, translucent, or reflective, and a) wherein an inner surface of the side wall of the well of one of the two, or more than two sample tabs has a height of a first value, and the inner surface of the side wall of the well of each of the other one, or more than one of the two, or more than two sample tabs has a height substantially equal to the first value, and wherein the top surface of the bottom wall of the well of one of the two, or more than two sample tabs has a length of a second value, and the top surface of the bottom wall of the well of each of the other one, or more than one of the two, or more than two sample tabs has a length less than or greater than the second value, or b) wherein an inner surface of the side wall of the well of one of the two, or more than two sample tabs has a height of a first value, and the inner surface of the side wall of the well of each of the other one, or more than one of the two, or more than two sample tabs has a height less than or greater than the first value, and wherein the top surface of the bottom wall of the well of one of the two, or more than two sample tabs has a length of a second value, and the top surface of the bottom wall of the well of each of the other one, or more than one of the two, or more than two sample tabs has a length substantially equal to the second value.

In addition, the present invention relates to a method for analyzing a set of two, or more than two samples, comprising:

i) adding one of the two, or more than two samples into the well of one of the two, or more than two sample tabs of the set described above;

ii) closing the cover plate of the sample tab from step i);

v) inserting the sample tab from step ii) into an instrument for analyzing the sample added in step i);

vi) analyzing the sample, and v) repeating steps i)–iv) for each of the other one, or more than one sample tab of the two, or more than two sample tabs.

In order to maintain the same optical path for samples of differing volumes, it is preferred that sample tabs having wells of differing diameters but of the same height are used, such as the sample tabs illustrated in FIGS. 12A–C, 13A–C or 14A–C. The use of a series or a set of sample tabs having wells of the same height but of different diameters allows the same length of optical path to be maintained for samples of different volume, and minimizing the air space for the samples of relatively lower volume, which would be present if sample tabs of the same height and diameter would be used for all of the samples of different volumes. By reducing or removing the air space within the sample well, air-sensitive samples, for example blood, may be more accurately analyzed.

FIGS. 15A–C, 16A–C and 17A–C show examples of a removable insert (11) according to the present invention. The volume of the well (10) may be adjusted by increasing, or by decreasing the diameter (d) of the well, as shown in FIGS. 15A–C, 16A–C or 17A–C. In addition, the volume of the well (10) may be decreased or increased by shortening or lengthening, respectively, the height (H) of the well (10). For example, FIGS. 16A–C illustrate a set of wells having a relatively longer height (H), and, consequently, larger volumes than the corresponding wells shown in FIGS. 15A–C. FIGS. 17A–C show inserts (11) comprising wells (10) having a relatively shorter height, and, consequently, smaller volumes than the corresponding wells shown in FIGS. 15A–C. By using set of inserts, or sample tabs that are characterized in comprising wells with a similar height (H), or set of wells having a similar diameter (d), measurements may be obtained that have reduced variability arising from non-sample sources. For example, by maintaining the height of the well constant the length of the light path through the sample, and the sample tab, is the sample over a range of sample volumes.

Accordingly, the present invention also provides a set of two, or more than two sample tabs, wherein each of the two, or more than two sample tabs comprises:

a base plate having a top surface, a bottom surface, and an opening extending from the top surface to the bottom surface, the top surface of the base plate defining a first plane, and the bottom surface of the base plate defining a second plane;

an insert comprising a well for insertion within the opening, the well having a side wall and a bottom wall, the insert disposed at least partly in the opening, wherein a top surface of the bottom wall defines a third plane, the third plane being above the first plane, coincident with the first plane, between the first and the second plane, coincident with the second plane, or below the second plane, and a cover plate connected to the base plate, the cover plate having an open position allowing a sample to be introduced in the well and a closed position in which a bottom surface of a section of the cover plate covers the well, wherein at a least a portion of one of the section of the cover plate and the bottom wall of the base plate is transparent or translucent, and at least a portion of the other of the section of the cover plate and the section of the bottom wall of the well is transparent, translucent or reflective, and a) wherein an inner surface of the side wall of the well of one of the two, or more than two sample tabs has a height of a first value, and the inner surface of the side wall of the well of each of the other one, or more than one of the two, or more than two sample tabs has a height substantially equal to the first value, and wherein the top surface of the bottom wall of the well of one of the two, or more than two sample tabs has a length of a second value, and the top surface of the bottom wall of the well of each of the other one, or more than one of the two, or more than two sample tabs has a length less than or greater than the second value, or b) wherein an inner surface of the side wall of the well of one of the two, or more than two sample tabs has a height of a first value, and the inner surface of the side wall of the well of each of the other one, or more than one of the two, or more than two sample tabs has a height less than or greater than the first value, and wherein the top surface of the bottom wall of the well of one of the two, or more than two sample tabs has a length of a second value, and the top surface of the bottom wall of the well of each of the other one, or more than one of the two, or more than two sample tabs has a length substantially equal to the second value.

In addition, the present invention also relates to a method for analyzing a set of two, or more than two samples, comprising:

i) adding one of the two, or more than two samples into the well of one of the two, or more than two sample tabs of the set defined above;

ii) closing the cover plate of the sample tab from step i);

vii) inserting the sample tab from step ii) into an instrument for analyzing the sample added in step i);

viii) analyzing the sample, and v) repeating steps i)–iv) for each of the other one, or more than one sample tab of the two, or more than two sample tabs.

In order to maintain the same optical path length for samples of differing volumes, replaceable inserts of differing diameters but of the same height should be used, such as the set of inserts illustrated in FIGS. 15A–C, the set of inserts shown in FIGS. 16A–C, or the set of inserts shown in FIGS. 17A–C. It is to be understood that additional members of each of these sets may be include that have a different well volume, providing that the height (H) remains constant. The use of a series of sample tabs having wells of the same height but of different diameters allows the length of the optical path to be maintained for samples of different volume by minimizing air space for the samples of relatively lower volume, which would be present if sample tabs of the same height and diameter would be used for all of the samples of different volumes.

The sample tab of the present invention may retain any sample for analysis using any suitable instrument, for example, but not limited to spectroscopic or microscopic analysis. Preferably the sample tab retains a fluid or semi-solid sample, for example, but not limited to non-biological, or biological samples. Examples of non-biological samples include, but are not limited to dairy products, for example, milk, cheese, cottage cheese, yoghurt, or ice cream, or beverages, or semi-solid foods. Examples of biological fluids include, but are not limited to whole blood, plasma, serum, synovial fluid, cerebral spinal fluid, urine, lymph, mucus, faeces, and semen.

The embodiments shown in FIGS. 2–6, 7A–B, 8A–D, 9A–D, 10A–D, 11, 12A–C, 13A–C, 14A–C, 15A–C, 16A–C, 17A–C and 18–20 are meant to be exemplary rather than limiting in any manner. Those of skill in the art will understand that modifications of the sample tab, base plate, cover plate and locking member, or a combination thereof may be made without departing from the spirit and scope of the present invention, and it is fully intended that such modifications are contemplated by the sample tab of the present invention.

The sample tab as described herein may be used within a spectrophotometer using standard methods as known in the art, for example as disclosed in U.S. Pat. Nos. 5,846,492, 6,268,910, WO 98/39634 (all of which are incorporated herein by reference). These references disclose the spectroscopic analysis of a biological fluid within a plastic or polyethylene container, for example blood bag tubing (U.S. Pat. No. 6,268,910), or a pipette tip (WO 98/39634; U.S. Pat. No. 5,846,492) However, it is to be understood that the sample tab as described herein may be readily adapted for other analytical uses including microscopic analysis.

The above description is not intended to limit the claimed invention in any manner. Furthermore, the discussed combination of features might not be absolutely necessary for the inventive solution.

All references are herein incorporated by reference.

The present invention has been described with regard to preferred embodiments. However, it will be obvious to persons skilled in the art that a number of variation and modifications can be made without departing from the scope of the invention as described herein.

The invention claimed is:

1. A sample tab comprising:

a base plate having a top surface and a bottom surface, the top surface of the base plate defining a first plane;

a well disposed on a section of the base plate, the well having a side wall and a bottom wall, the side wall of the well comprising one, or more than one overflow opening, and the side wall of the well being surrounded by a containment wall, wherein the containment wall and the side wall define an overflow channel therebetween, and wherein a top surface of the bottom wall defines a second plane, the second plane disposed above or below the first plane;

a cover plate hingedly connected to the base plate, the cover plate having an open position allowing a sample to be introduced into the well and a closed position in which a bottom surface of a section of the cover plate covers the well, and a locking member for locking the cover plate to the base plate when the cover plate is in the closed position, wherein at least a portion of the bottom wall of the well is transparent or translucent, and wherein at least a portion of one of the section of the cover plate and the section of the base plate is transparent or translucent, and at least a portion of the other of the section of the cover plate and the section of the base plate is transparent, translucent or reflective, or wherein the bottom wall of the well is defined by the section of the base plate, and wherein at least a portion of one of the section of the cover plate and the section of the base plate is transparent or translucent, and at least a portion of the other of the section of the cover plate and the section of the base plate is transparent, translucent, or reflective.

2. The sample tab of claim 1, wherein the locking member comprises one, or more than one clip for locking the cover plate to the base plate when the cover plate is in the closed position.

3. The sample tab of claim 1, wherein the locking member is on the cover plate, the base plate, or both the cover plate and the base plate.

4. The sample tab of claim 1, wherein the locking member is an element for frictionally engaging an outer portion of the containment wall when the cover plate is in the closed position.

5. The sample tab of claim 4, wherein the containment wall is circular, and the locking member is a circular ring.

6. The sample tab of claim 1, wherein the containment wall comprises a sealing member on its upper surface.

7. The sample tab of claim 6, wherein the sealing member is an O ring.

8. The sample tab of claim 6, wherein the sealing member is a pliable material integral with the containment wall.

9. The sample tab of claim 1, wherein the side wall of the well is circular.

10. The sample tab of claim 1, wherein the containment wall is circular.

11. The sample tab of claim 1, wherein at least a portion of the bottom wall of the well is transparent or translucent, at least a portion of the section of the cover plate is reflective, and at least a portion of the section of base plate is transparent or translucent.

12. The sample tab of claim 1, wherein at least a portion of the bottom wall of the well is transparent or translucent, at least a portion of the section of the cover plate is transparent or translucent, and at least a portion of the section of the base plate is transparent or translucent.

13. The sample tab of claim 1, wherein at least a portion of the bottom wall of the well is transparent or translucent, at least a portion of the section of the cover plate is transparent or translucent, and at least a portion of the section of the base plate is reflective.

14. The sample tab of claim 1, wherein the bottom wall of the well is transparent or translucent, the section of the cover plate is reflective, and the section of the base plate is transparent or translucent.

15. The sample tab of claim 1, wherein the bottom wall of the well is transparent or translucent, the section of the cover plate is transparent or translucent, and the section of the base plate is transparent or translucent.

16. The sample tab of claim 1, wherein the bottom wall of the well is transparent or translucent, the section of the cover plate is transparent or translucent, and the section of the base plate is reflective.

17. The sample tab of claim 1, wherein the bottom wall of the well is defined by the section of the base plate, at least a portion of the section of the cover plate is reflective, and at least a portion of the section of the base plate is transparent or translucent.

18. The sample tab of claim 1, wherein the bottom wall of the well is defined by the section of the base plate, at least a portion of the section of the cover plate is transparent or translucent, and at least a portion of the section of the base plate is transparent or translucent.

19. The sample tab of claim 1, wherein the bottom wall of the well is defined by the section of the base plate, at least a portion of the section of the cover plate is transparent or translucent, and at least a portion of the section of the base plate is reflective.

20. The sample tab of claim 1, wherein the bottom wall of the well is defined by the section of the base plate, the section of the cover plate is reflective, and the section of the base plate is transparent or translucent.

21. The sample tab of claim 1, wherein the bottom wall of the well is defined by the section of the base plate, the section of the cover plate is transparent or translucent, and the section of the base plate is transparent or translucent.

22. The sample tab of claim 1, wherein the bottom wall of the well is defined by the section of the base plate, the section of the cover plate is transparent or translucent, and the section of the base plate is reflective.

23. The sample tab of claim 1, wherein the second plane is below the first plane.

24. The sample tab of claim 1, wherein the second plane is above the first plane.

25. The sample tab of claim 1, wherein the side and bottom walls of the well are defined by the base plate.

26. The sample tab of claim 25, wherein the side wall of the well extends above the top surface of the base plate.

27. A method for analyzing a sample, comprising:
   i) adding a sample into the well of the sample tab according to claim 1,
   ii) closing the cover plate of the sample tab,
   iii) inserting the sample tab into an instrument for analyzing the sample, and
   iv) analyzing the sample.

28. The method according to claim 27, wherein, in the step of inserting (step iii)), the sample tab is placed in a horizontal position within a sample holder of the instrument, and wherein the sample is analyzed by projecting electromagnetic radiation through the well in a direction substantially perpendicular to the position of the sample tab.

29. A sample tab comprising:
   a base plate having a top surface, a bottom surface, and an opening extending from the top surface to the bottom surface, the top surface of the base plate defining a first plane, and the bottom surface of the base plate defining a second plane;
   an insert comprising a well and a containment wall, for insertion within the opening, the well having a side wall and a bottom wall, the insert disposed at least partly in the opening, the side wall of the well comprising one, or more than one overflow opening, and the side wall of the well being surrounded by the containment wall, wherein the containment wall and the side wall define a containment channel therebetween, and wherein a top surface of the bottom wall defines a third plane, the third plane being above the first plane, coincident with the first plane, between the first and the second plane, coincident with the second plane, or below the second plane;
   a cover plate connected to the base plate, the cover plate having an open position allowing a sample to be introduced in the well and a closed position in which a bottom surface of a section of the cover plate covers the well, and
   a locking member for locking the cover plate to the base plate when the cover plate is in the closed position,
   wherein at least a portion of one of the section of the cover plate and the bottom wall of the well is transparent or translucent, and at least a portion of the other of the section of the cover plate and the bottom wall of the well is transparent, translucent or reflective.

30. A set of two, or more than two sample tabs, wherein each of the two, or more than two sample tabs comprises:
   a base plate having a top surface and a bottom surface, the top surface of the base plate defining a first plane;
   a well disposed on a section of the base plate, the well having a side wall and a bottom wall, the side wall of the well comprising one, or more than one overflow opening, and the side wall of the well being surrounded by a containment wall, wherein the containment wall and the side wall define an overflow channel therebetween, and wherein a top surface of the bottom wall defines a second plane, the second plane disposed above the first plane, below the first plane, or coincident with the first plane;

a cover plate hingedly connected to the base plate, the cover plate having an open position allowing a sample to be introduced into the well and a closed position in which a bottom surface of a section of the cover plate covers the well, and a locking member for locking the cover plate to the base plate when the cover plate is in the closed position, wherein at least a portion of the bottom wall of the well is transparent or translucent, and wherein at least a portion of one of the section of the cover plate and the section of the base plate is transparent or translucent, and at least a portion of the other of the section of the cover plate and the section of the base plate is transparent, translucent or reflective, or wherein the bottom wall of the well is defined by the section of the base plate, and wherein at least a portion of one of the section of the cover plate and the section of the base plate is transparent or translucent, and at least a portion of the other of the section of the cover plate and the section of the base plate is transparent, translucent, or reflective, and a) wherein an inner surface of the side wall of the well of one of the two, or more than two sample tabs has a height of a first value, and the inner surface of the side wall of the well of each of the other one, or more than one of the two, or more than two sample tabs has a height substantially equal to the first value, and wherein the top surface of the bottom wall of the well of one of the two, or more than two sample tabs has a length of a second value, and the top surface of the bottom wall of the well of each of the other one, or more than one of the two, or more than two sample tabs has a length less than or greater than the second value, or b) wherein an inner surface of the side wall of the well of one of the two, or more than two sample tabs has a height of a first value, and the inner surface of the side wall of the well of each of the other one, or more than one of the two, or more than two sample tabs has a height less than or greater than the first value, and wherein the top surface of the bottom wall of the well of one of the two, or more than two sample tabs has a length of a second value, and the top surface of the bottom wall of the well of each of the other one, or more than one of the two, or more than two sample tabs has a length substantially equal to the second value.

31. A method for analyzing a set of two, or more than two samples, comprising:

i) adding one of the two, or more than two samples into the well of one of the two, or more than two sample tabs of the set according to claim 30;

ii) closing the cover plate of the sample tab from step i);

iii) inserting the sample tab from step ii) into an instrument for analyzing the sample added in step i);

iv) analyzing the sample, and v) repeating steps i)–iv) for each of the other one, or more than one sample tab of the two, or more than two sample tabs.

32. A set of two, or more than two sample tabs, wherein each of the two, or more than two sample tabs comprises:

a base plate having a top surface, a bottom surface, and an opening extending from the top surface to the bottom surface, the top surface of the base plate defining a first plane, and the bottom surface of the base plate defining a second plane;

an insert comprising a well and a containment wall for insertion within the opening, the well having a side wall and a bottom wall, the insert disposed at least partly in the opening, the side wall of the well comprising one, or more than one overflow opening, and the side wall of the well being surrounded by the containment wall, wherein the containment wall and the side wall define a containment channel therebetween, and wherein a top surface of the bottom wall defines a third plane, the third plane being above the first plane, coincident with the first plane, between the first and the second plane, coincident with the second plane, or below the second plane;

a cover plate connected to the base plate, the cover plate having an open position allowing a sample to be introduced in the well and a closed position in which a bottom surface of a section of the cover plate covers the well, and a locking member for locking the cover plate to the base plate when the cover plate is in the closed position, wherein at a least a portion of one of the section of the cover plate and the bottom wall of the well is transparent or translucent, and at least a portion of the other of the section of the cover plate and the bottom wall of the well is transparent, translucent or reflective, and a) wherein an inner surface of the side wall of the well of one of the two, or more than two sample tabs has a height of a first value, and the inner surface of the side wall of the well of each of the other one, or more than one of the two, or more than two sample tabs has a height substantially equal to the first value, and wherein the top surface of the bottom wall of the well of one of the two, or more than two sample tabs has a length of a second value, and the top surface of the bottom wall of the well of each of the other one, or more than one of the two, or more than two sample tabs has a length less than or greater than the second value, or b) wherein an inner surface of the side wall of the well of one of the two, or more than two sample tabs has a height of a first value, and the inner surface of the side wall of the well of each of the other one, or more than one of the two, or more than two sample tabs has a height less than or greater than the first value, and wherein the top surface of the bottom wall of the well of one of the two, or more than two sample tabs has a length of a second value, and the top surface of the bottom wall of the well of each of the other one, or more than one of the two, or more than two sample tabs has a length substantially equal to the second value.

33. A method for analyzing a set of two, or more than two samples, comprising:

i) adding one of the two, or more than two samples into the well of one of the two, or more than two sample tabs of the set according to claim 32;

ii) closing the cover plate of the sample tab from step i);

v) inserting the sample tab from step ii) into an instrument for analyzing the sample added in step i);

vi) analyzing the sample, and v) repeating steps i)–iv) for each of the other one, or more than one sample tab of the two, or more than two sample tabs.

* * * * *